United States Patent [19]

Kauer

[11] 4,104,275

[45] Aug. 1, 1978

[54] HETEROARYL CROWN ETHERS

[75] Inventor: James Charles Kauer, Kennett Square, Pa.

[73] Assignee: E. I. Du Pont de Nemours and Company, Wilmington, Del.

[21] Appl. No.: 764,580

[22] Filed: Feb. 1, 1977

Related U.S. Application Data

[63] Continuation of Ser. No. 615,184, Sep. 19, 1975, Pat. No. 4,024,158.

[51] Int. Cl.$^2$ ............................................. C07D 323/00
[52] U.S. Cl. ........................... 260/297 B; 260/294.9; 260/295 F; 260/295 T; 260/295.5 B; 260/295.5 T; 260/296 B; 260/296 T; 260/297 T; 260/332.2 A; 260/332.3 H; 260/340.3
[58] Field of Search ............ 260/297 B, 297 T, 296 B, 260/332.2 A, 332.3 H, 295 F, 295 T, 295.5 B, 340.3, 294.9

[56] References Cited

U.S. PATENT DOCUMENTS

| | | | |
|---|---|---|---|
| 3,687,978 | 8/1972 | Pedersen | 260/340.3 |
| 3,965,116 | 6/1976 | Cram | 260/338 |

*Primary Examiner*—Alan L. Rotman
*Attorney, Agent, or Firm*—Anthony P. Mentis

[57] ABSTRACT

Aroylcrownethers are complexing agents for metals, dispersing agents for carbon black and preferred ones are antiviral agents. Examplary is 4'-benzoylbenzo-18-crown-6 of the formula

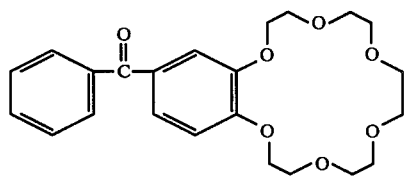

14 Claims, No Drawings

HETEROARYL CROWN ETHERS

This is a continuation of application Ser. No. 615,184, filed Sept. 19, 1975, now U.S. Pat. No. 4,024,158.

BACKGROUND OF THE INVENTION

1. Field of the Invention

Certain aroylcrownethers are complexing agents for metals and dispersing agents for carbon black. The preferred compounds show activity in vitro against a number of picornaviruses.

2. Prior Art

Pedersen J. Am. Chem. Soc. 89 7017 (1967) describes cyclic polyethers derived from aromatic vicinal diols by reaction with α,ω-alkylene diprimary dihalides containing oxygen atoms in the chain, in the presence of strong bases. In particular, when catechol, sodium hydroxide and 1,14-dichloro-3,6,9,12-tetraoxatetradecane are reacted, there is obtained the compound

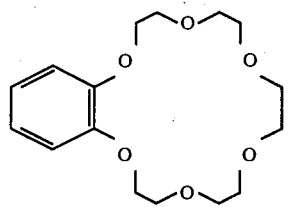

2′,3′-benzo-1,4,7,10,13,16-hexaoxacyclooctadec-2-ene. This compound is named 2,3,5,6,8,9,11,12,14,15-decahydro-1,4,7,10,13,16-benzohexaoxacyclooctadecin by Chemical Abstracts. A more convenient trivial terminology, which is employed herein, is to identify the compound as a "crown" compound wherein the total number of atoms in the macrocylic ring is designated by an antecedent number and the total number of oxygen atoms by a subsequent number. Using this terminology, the above compound is called benzo-18-crown-6.

Similarly 2,3-naphtho-18-crown-6 is obtained from 2,3-dihydroxynaphthalene by the procedure above.

Kopolow et al., Macromolecules 6 133 (1973) have described the 4-acetyl derivative of benzo-18-crown-6.

DESCRIPTION OF THE INVENTION

The invention is a compound of the general formula

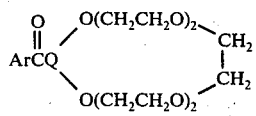

wherein

Ar is phenyl, naphthyl, thienyl, pyridyl or furyl, each with up to two substituents of alkyl of 1-10 carbons, alkoxy of 1-10 carbons, halogen, carboxy or cyano groups;

Q is

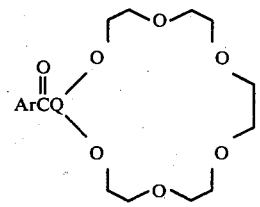

in which R is fluorine, chlorine, bromine, nitro, amino, or alkyl of 1-10 carbons; and $n = 0$ to 2.

The general formula above can also be written more pictorially as

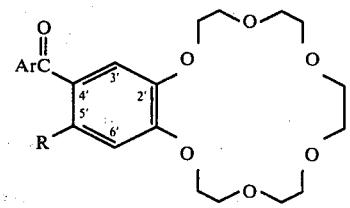

Preferred are compounds where the Ar group has a halogen substituent or an alkyl or alkoxy substituent each of 1-6 carbons, and R is an alkyl group of 1-6 carbons on the 5-position of the phenyl ring or the 7-position of the naphthyl ring. Most preferred are compounds where R is methyl.

The most preferred Ar groups for antiviral activity are phenyl, p-tolyl, o-fluorophenyl, p-fluorophenyl, p-chlorophenyl, 3-pyridyl, 2- and 3-furyl and 2-methyl-5-thienyl in compounds of the formula wherein R is H, methyl or amino.

The compounds of the invention are useful as dispersing agents for carbon black and complexing agents for metals. They can also be employed as the polycyclic ethers in the process of U.S. Pat. No. 3,546,318 to provide improved scratch resistant coatings.

Further, they are capable of preventing the infection of HeLa cells in vitro by a wide spectrum of picornaviruses and in particular rhinoviruses.

The compounds of the invention, when R is hydrogen, can be made by the Friedel-Crafts reaction of benzo-18-crown-6 with the appropriate aroyl chloride (ArCOCl) or with aroylhexafluoroantimonate (ArCOSbF$_6$), under conventional conditions. These products may, in turn, be nitrated to introduce an NO$_2$ substituent, which on catalytic reduction gives the corresponding amine (R=NH$_2$).

When R is other than hydrogen, the Friedel-Crafts or other conventional electrophilic reaction can be used to insert a substituent on the benzo-18-crown-6 compound. This substituted compound is then reacted with the aroyl reactant as above.

Alternatively, a substituted catechol can be condensed with 1,14-dichloro-3,6,9,12-tetraoxatetradecane to form the crown compound. Thus, a 4′-pyridoylcatechol (from 3,4-dimethoxybenzaldehyde with the appropriate pyridyllithium solution followed by acidic hydrolysis of the ether groups) froms a 4'-pyridoylbenzo-18-crown-6.

SPECIFIC EMBODIMENTS OF THE INVENTION

In the following illustrative examples all parts are by weight and all tempertures are Centigrade unless otherwise specified.

EXAMPLE 1

4'-Benzoylbenzo-18-crown-6

A mixture of 14.818 g of anhydrous aluminum chloride and 300 ml of dry 1,2-dichloroethane was cooled in ice, and a solution of 15.60 g of bezoyl chloride in 1,2-dichloroethane was added followed by a solution of 11.12 g of benzo-18-crown-6 in 20 ml of 1,2-dichloroethane. The mixture was stirred for 60 hours and was decomposed by the addition of 100 g of ice. After stirring for 30 min., the organic layer was separated and was stirred for 4 hrs with 20% potassium carbonate solution. (A longer washing period was subsequently found to be desirable.) The organic layer was dried with magnesium sulfate and solvent was evaporated. The residue was dissolved in 100 ml of ether and rapidly crystallized. Recrystallization from ethanol produced 5.13 g of white crystals which melted at 112.2°–113.8°.

Anal. Calcd for $C_{23}H_{28}O_7$: C, 66.33; H, 6.78. Found: C, 66.53; H, 6.80.

EXAMPLE 2

4'-p-Chlorobenzoylbenzo-18-crown-6

A stirred suspension of 5.778 g of anhydrous aluminum chloride in 150 ml of 1,2-dichloroethane was chilled in ice. A solution of 7.60 g of p-chlorobenzoyl chloride in 20 ml of 1,2-dichloroethane was added followed by a solution of 4.51 g of benzo-18-crown-6 in 20 ml of 1,2-dichloroethane. The mixture was stirred for 3 days and was then decomposed with 30 g of ice. The organic layer was separated. The water layer was extracted with dichloromethane. The combined organic layers were stirred overnight with 10% potassium carbonate. The organic layer was dried over magnesium sulfate, and solvent was removed under reduced pressure to leave 7.56 g of a tan solid residue. This was triturated with ether and filtered. The resulting solid was recrystallized from ethanol to give 2.986 g of silky leaflets which melted at 142.5°–144.1°.

Anal. Calcd for $C_{23}H_{27}ClO_7$: C, 61.26; H, 6.04; Cl, 7.86. Found: C, 61.51; H, 6.06; Cl, 7.77.

EXAMPLE 3

4'-p-Fluorobenzoylbenzo-18-crown-6

A stirred suspension of 6.330 g of anhydrous aluminum chloride in 100 ml of 1,2-dichloroethane was chilled in ice. A solution of 7.53 g of p-fluorobenzoyl chloride in 1,2-dichloroethane was added followed by a solution of 4.95 g of benzo-18-crown-6 in 50 ml of 1,2-dichloroethane. The mixture was stirred for 2 days and was then decomposed with 150 g of ice. The organic layer was separated. The water layer was extracted with dichloromethane. The combined organic layers were stirred for 4 days with 10% potassium carbonate. The organic layer was dried over magnesium sulfate, and solvent was removed under reduced pressure to leave 5.74 g of an oil which crystallized. This was triturated with ether and filtered. The resulting solid was recrystallized from 75 ml of ethanol to give 2.382 g of white crystals which melted at 126.8°–128.5°.

Anal. Calcd for $C_{23}H_{27}FO_7$: C, 63.58; H, 6.27; F, 4.37. Found: C, 63.98; H, 6.44; F, 4.48.

EXAMPLE 4

4'-(3,4-Dichlorobenzoyl)benzo-18-crown-6

A stirred suspension of 5.389 g of anhydrous aluminum chloride in 100 ml of 1,2-dichloroethane was chilled in ice. A solution of 8.46 g of 3,4-dichlorobenzoyl chloride in 1,2-dichloroethane was added followed by a solution of 4.21 g of benzo-18-crown-6 in 1,2-dichloroethane. The mixture was stirred for 4 days and was then decomposed with 150 g of ice. The organic layer was separated. The water layer was extracted with dichloromethane. The combined organic layers were stirred for 2 days with 10% potassium carbonate. The organic layer was dried over magnesium sulfate, and solvent was removed under reduced pressure to leave an amber oil. This was trituated with ether and filtered. The resulting solid was recrystallized from ethanol/acetone to give 1.265 g of off-white crystals. Recrystallization produced crystals which melted at 152°–153.4°.

Anal. Calcd for $C_{23}H_{26}Cl_2O_7$: C, 56.92; H, 5.40; Cl, 14.61. Found: C, 57.16; H, 5.54; Cl, 14.21.

EXAMPLE 5

4'-Benzoyl-5'-Methylbenzo-18-crown-6

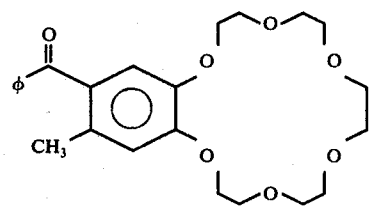

A suspension of 4.0 g (0.03 mol) of aluminum chloride in 50 ml of DCE (1,2-dichloroethane) was stirred magnetically under nitrogen and cooled in an ice bath. Benzoyl chloride (4.65 g, 0.033 mol) in 25 ml of DCE was added dropwise. The mixture was stirred for 1 hr at 0°, then warmed to room temperature. A solution of 3.26 g (0.01 mol) of 4'-methylbenzo-18-crown-6 ether [U. Takaki, T. E. Hogen-Esch, and J. Smid. *J. Amer. Chem. Soc.*, 93, 6760 (1971)] in 25 ml of DCE was added dropwise. The mixture was stirred overnight, then poured into water. The layers were separated and the water layer extracted three times with methylene chloride. The organic layers were combined and washed with saturated brine, dried over magnesium sulfate and stripped to give a yellow liquid. This was dissolved in ether, washed twice with 100 ml portions of 2N sodium hydroxide, dried and stripped to give 6.3 g of a yellow oil containing crystals. Recrystallization from ether, then ethyl acetate-hexane gave 2.1 g (49%) of fine white needles, mp 88.5°–89°; infrared (nujol) 1660 (C=OO, 1600 (aromatic C=C), 1120 (ArOC), 1090 (COC) cm$^{-1}$; nmr (CDCl$_3$) δ 2.23 (s, 3H, —CH$_3$), 3.58 (s), 3.63 (s), 3.65 (s), 3.85 (m, total 20H, macro ring), 6.70 (d), 7.35 (m, total 7H, aromatic protons).

Anal. Calcd for $C_{24}H_{30}O_7$: C, 66.96; H, 7.02. Found: C, 67.35; H, 7.17; C, 67.19; H, 7.02.

EXAMPLE 6

4'-(1-Naphthoyl)-5'-Methylbenzo-18-crown-6

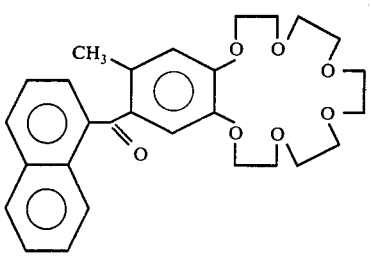

Aluminum chloride (4.0 g, 0.03 mol) was suspended in 50 ml of 1,2-dichloroethane (DCE) in a magnetically stirred flask under nitrogen and cooled in an ice bath. A solution of 6.29 g (0.033 mol) of 1-naphthoyl chloride in 25 ml of DCE was added dropwise. The mixture was stirred for 1 hr at 0°, then allowed to warm to room temperature. A solution of 3.26 g (0.01 mol) of 4'-methylbenzo-18-crown-6 in 25 ml of DCE was added dropwise. The mixture was stirred overnight at room temperature. The mixture was poured into water and stirred for 15 min. The layers were separated, and the aqueous layer extracted three times with methylene chloride. The combined organic layers were washed once with water and twice with 2N sodium hydroxide solution. The solution was dried over magnesium sulfate, filtered and stripped to give 8.4 g of a brown oil. This oil was taken with 150 ml of ether and stirred vigorously under nitrogen with 150 ml of 2N sodium hydroxide solution for 3 hrs. The layers were separated, taking a dense oil with the water layer. The aqueous phase was extracted thrice with methylene chloride. The organic layers were combined and dried over magnesium sulfate. Filtration and removal of solvent gave 5.03 g of a brown viscous oil which solidified on standing. Recrystallization from ethyl acetate-hexane (from an oil) gave 3.27 g of a greenish solid, mp 82°-85°. This was dissolved in hot acetonitrile and seeded with a crystal produced by rapid chilling of a small sample. Chilling of the solution, filtration, and washing with cold acetonitrile gave 2.56 g of fine white needles, of the title compound as an acetonitrile complex, mp 80°-93°; infrared (nujol) 2250 (C≡N), 1640 (C=O), 1600 (aromatic C=C), 1120 (ArOC) cm$^{-1}$; nmr (CDCl$_3$) δ 1.95 (s, 2.7H, CH$_3$CN), 2.42 (s, 3H, —CH$_3$), 3.67 (s), 3.72 )s), 3.10 (m, total 20H, macro ring), 6.77, 6.95 (s), 7.5 (m), 7.0 (m, total 9H, aromatic protons).

EXAMPLE 7

4'-o-Toluoylbenzo-18-crown-6

A mixture of 6.00 g of anhydrous aluminum chloride and 100 ml of dry 1,2-dichloroethane was cooled in ice, and a solution of 6.95 g of o-toluoyl chloride in 20 ml of 1,2-dichloromethane was added followed by a solution of 3.52 g of benzo-18-crown-6 in 20 ml of 1,2-dichloroethane. The mixture was stirred under nitrogen for 3 days and was decomposed by the addition of 30 g of ice. After stirring 30 minutes, the organic layer was separated. The aqueous layer was washed with methylene chloride. The combined organic layers were evaporated and the residue was dissolved in 300 ml of ether and stirred for 3 hrs with 100 ml of 8% aqueous sodium hydroxide solution. A white precipitate formed in the resulting mixture. Infrared spectroscopy indicated that it was the desired product (C=O at 1645 cm$^{-1}$). The mixture was filtered to give 3.304 g of solid. The ether layer of the filtrate was separated and evaporated to dryness. The residue was dissolved in methylene chloride, dried over magnesium sulfate, and solvent was removed by evaporation. The residue was stirred with ether to give an additional 0.524 g of white crystals with an infrared spectrum identical with the previously isolated solid. The combined solids were recrystallized from 15 ml of ethanol (after decolorizing with Darco) to produce 3.3 g of white crystals of o-toluoylbenzo-18-crown-6 which melted at 107.1°-109.5°.

Anal. Calcd for C$_{24}$H$_{30}$O$_7$: C, 66.96; H, 7.02. Found: C, 66.79; H, 7.15.

EXAMPLE 8

4'-α-Naphthoylbenzo-18-crown-6

To a cold mixture of 6.00 g of anhydrous aluminum chloride and 100 ml of anhydrous 1,2-dichloroethane was added a solution of 8.58 g of α-naphthoyl chloride followed by a solution of 4.69 g of benzo-18-crown-6 (both in 1,2-dichloroethane). The method of Example 3 was followed and produced 10.1 g of a white powder which contained an anhydride impurity (ir spectroscopy). This crude solid was suspended in 200 ml of ether and was stirred for 2 days with 200 ml of 8% aqueous sodium hydroxide.

Ether was evaporated from the resulting mixture and the residue was extracted twice with 100 ml portions of methylene chloride. The combined organic layers were dried (MgSO$_4$) and evaporated to produce 5.547 g of a yellow oil which was stirred with 100 ml of ether. The resulting white crystals (3.89 g) were recrystallized from 50 ml of acetone to produce 2.28 g of white crystals of 4'-α-naphthoylbenzo-18-crown-6 which melted at 108.2°-111.4°.

Anal. Calcd for C$_{27}$H$_{30}$O$_7$: C, 69.51; H, 6.48. Found: C, 69.74; H, 6.51.

EXAMPLE 9

4'-(2-Thienoyl)benzo-18-crown-6

A mixture of 6.00 g of anhydrous aluminum chloride and 100 ml of dry 1,2-dichloroethane was cooled in ice and a solution of 6.60 g of thiophene-2-carbonyl chloride in 20 ml of 1,2-dichloroethane was added followed by a solution of 4.69 g of benzo-18-crown-6 in 20 ml of 1,2-dichloroethane. The mixture was stirred under nitrogen for 3 days and was decomposed by the addition of 30 g of ice. After stirring for 30 minutes the organic layer was separated and the aqueous layer was washed with methylene chloride. The combined organic layers were evaporated and the residue was dissolved in 300 ml of ether and stirred for 3 hrs with 8% aqueous sodium hydroxide solution. The resulting mixture was filtered and the organic layer was separated and evaporated. The residue was dissolved in methylene chloride, dried with magnesium sulfate, and evaporated. The residue was an amber oil (6.60 g) which was triturated with ether. The resulting white solid (5.13 g) was filtered off and washed with ether. It was recrystallized from ethanol to produce 4.62 g of white crystals which melt at 105.1°-108.4°. The infrared spectrum exhibited a C=O absorption at 1640 cm$^{-1}$.

Anal. Calcd for C$_{21}$H$_{26}$O$_7$S: C, 59.70; H, 6.20; S, 7.59. Found: C, 60.09; H, 6.28; S, 7.57.

Other compounds of the invention are shown in Table I. They were prepared from appropriate starting materials by methods used in crown compound preparation. The compound of Example 20 was made starting with 3-methylcatechol and pentaethylene glycol dichloride followed by benzyol chloride-aluminum chloride treatment on the 3'-methylbenzo-18-crown-6. The compound of Example 21 was prepared using benzoylhexafluoroantimonate on 4'-chlorobenzo-18-crown-6 (obtained from 4-chlorocatechol and pentaethylene glycol dichloride). The compound of Example 27 was prepared similarly from 4'-bromobenzo-18-crown-6, which was made by bromination of benzo-18-crown-6.

TABLE I (Q=benzo)

| Example | Ar | R | mp °C | Elemental Analysis For | Calc'd | Found |
|---|---|---|---|---|---|---|
| 10 | 3-methylphenyl | H | 75.1–77.5 | C<br>H | 66.96<br>7.02 | 67.24, 66.87<br>6.93, 6.97 |
| 11 | 2-ethylphenyl | H | 115–116 | C<br>H | 67.55<br>7.26 | 67.61<br>7.29 |
| 12 | 4-ethylphenyl | H | 104.5–106.5 | C<br>H | 67.55<br>7.26 | 67.79<br>7.24 |
| 13 | 4-n-C$_5$H$_{11}$-phenyl | H | 62.5–64 | C<br>H | 69.11<br>7.87 | 68.75<br>7.64 |
| 14 | 4-n-C$_6$H$_{13}$-phenyl | H | 70.0–70.8 | C<br>H | 69.57<br>8.05 | 69.89<br>8.06 |
| 15 | 4-n-C$_5$H$_{11}$O-phenyl | H | 83.7–84.9 | C<br>H | 66.91<br>7.92 | 67.19<br>7.32 |
| 16 | 4-NC-phenyl | H | 168–171 | C<br>H<br>N | 65.29<br>6.16<br>3.17 | 65.09<br>6.27<br>3.56 |
| 17 | 5-methyl-2-thienyl | H | 78.4–79.3 | C<br>H<br>S | 61.53<br>6.47<br>7.35 | 60.78, 60.87<br>6.51, 6.53<br>7.17 |
| 18 | 2-furyl | H | 66.1–68.4 | C<br>H | 62.06<br>6.45 | 62.27, 62.31<br>6.47, 6.53 |
| 19 | 2-furyl | H | 81.0–81.8 | C<br>H | 62.06<br>6.45 | 62.27<br>6.45 |
| 20 | phenyl | CH$_3$<br>(3'-position) | (Oil) | | | |
| 21 | phenyl | Cl | 104–106 | | | |
| 22 | 4-CH$_3$-phenyl | CH$_3$ | 86–86.5 | C<br>H | 67.55<br>7.26 | 67.73<br>7.00 |
| 23 | 2-furyl | CH$_3$ | 72–74 | C<br>H | 62.85<br>6.71 | 63.21, 62.44<br>6.71, 6.72 |
| 24 | 4-F-phenyl | CH$_3$ | 82.5–84.5 | C<br>H<br>F | 64.27<br>6.02<br>4.24 | 64.42, 64.71<br>6.55, 6.59<br>4.24 |
| 25 | 2-thienyl | CH$_3$ | 93–108 | C<br>H<br>S | 58.13<br>6.65<br>7.06 | 57.87, 58.35<br>6.52, 6.79<br>7.15 |
| | (monohydrate) | | | | | |
| 26 | phenyl | C$_2$H$_5$— | 96–97 | C<br>H | 67.55<br>7.26 | 67.61, 67.66<br>7.11, 7.08 |
| 27 | phenyl | Br | 114–116 | C<br>H | 55.77<br>5.49 | 55.93, 55.81<br>5.59, 5.44 |
| 28 | 3-methylphenyl | H | 100.1–103.2 | C<br>H | 66.96<br>7.02 | 67.14<br>7.17 |
| 29 | 2-thienyl | CH$_3$ | 98–100 | C<br>H | 60.53<br>6.47 | 60.50<br>6.38 |

TABLE I-continued (Q=benzo)

| Example | Ar | R | mp °C | Elemental Analysis For | Calc'd | Found |
|---|---|---|---|---|---|---|
| 30 | (furyl) (Monohydrate) | CH₃ | 99–102 | C<br>H | 60.26<br>6.90 | 60.05<br>6.86 |
| 31 | CH₃-(thienyl) | CH₃ | 104.5–106 | C<br>H<br>S | 61.31<br>6.71<br>7.12 | 61.26<br>6.65<br>7.12 |
| 32 | o-Cl-C₆H₄ | CH₃ | 134–136.5 | C<br>H | 62.00<br>6.29 | 62.25<br>6.38 |
| 33 | Cl-C₆H₄- | CH₃ | 96–97 | C<br>H<br>Cl | 62.06<br>6.29<br>7.63 | 62.12<br>6.39<br>6.47 |
| 34 | o-F-C₆H₄ | CH₃ | 107–109 | C<br>H<br>F | 64.27<br>6.52<br>4.24 | 64.56<br>6.50<br>4.27 |
| 35 | m-F-C₆H₄ | CH₃ | 89.5–91 | C<br>H<br>F | 64.27<br>6.52<br>4.24 | 64.39<br>6.46<br>4.38 |
| 36 | 2,3-F₂-C₆H₃ | CH₃ | 105.5–107.5 | C<br>H | 61.79<br>6.05 | 61.92<br>6.08 |
| 37 | t-C₄H₉-C₆H₄- | H | 61.4–68.2 | C<br>H | 68.62<br>7.68 | 68.21<br>7.83 |
| 38 | CH₃O-C₆H₄- | H | 117.9–117.4 | C<br>H | 64.76<br>6.77 | 64.39<br>6.68 |

Using the procedures described, the following additional compounds of the invention can be obtained: 5'-n-propyl-4'-benzo-18-crown-6; 5'-ethyl-4'-p-chlorobenzoylbenzo-18-crown-6; 5'-n-butyl-4'-benzoylbenzo-18-crown-6; 5'-n-decyl-4'-benzoylbenzo-18-crown-6; 4'-p-chloro-m-toluoylbenzo-18-crown-6; 5'-methyl-4'-p-chloro-m-toluoylbenzo-18-crown-6; 5'-t-butyl-4'-m-toluoylbenzo-18-crown-6; 4'-p-butylbenzoylbenzo-18-crown-6; 4'-p-anisoyl-m-chlorobenzo-18-crown-6; 4'-ethoxybenzoylbenzo-18-crown-6; 5'-ethyl-4'-α-naphthoyl-18-crown-6; 5'-methyl-4'-β-naphthoyl-18-crown-6; 5'-methyl-4'-m-bromobenzoyl-18-crown-6; 5'-methyl-4'-p-nitrobenzoyl-18-crown-6; and 4'-(3,4-methylenedioxy)benzoyl-18-crown-6.

EXAMPLE 39

5'-Benzoylnaphtho-18-crown-6

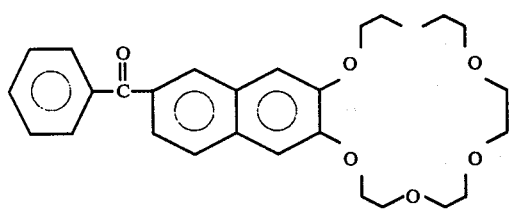

The general procedure of Example 1 was repeated except that 8.15 g of 2,3-naphtho-18-crown-6, 12.63 g of benzoyl chloride and 12 g of aluminum chloride in 100 ml of 1,2-dichloroethane was reacted for 3 days. There was obtained 6.4 g of 5'-benzoylnaphtho-18-crown-6 mp 145.2°–147.4°.

Anal Calcd for C₂₇H₃₀O₇; C, 69.51; H, 6.48. Found: C, 69.92; H, 6.45.

EXAMPLE 40

4'-(2-Pyridylcarbonyl)benzo-18-crown-6, also named as 1-(2,3,5,6,8,9,11,12,14,15-decahydro-1,4,7,10,13,16-benzohexaoxacyclooctadecin-18-yl)-1-(2-pyridyl)-methanone A stirred solution of 187.5 ml of 1.6 M solution of butyllithium in hexane was cooled to −40° under nitrogen and 39.5 g (0.25 M) of 2-bromopyridine in 100 ml of ether added dropwise. The mixture was stirred 15 minutes at −40° and a solution of 41.5 g (0.25 M) of 3,4-dimethoxybenzaldehyde in 200 ml of ether added. After stirring at −15° for 45 minutes, the mixture was poured into 500 g ice/100 ml conc. HCl. The separated aqueous layer was made alkaline with conc. NH₄OH, extracted with methylene chloride and the dried extract concentrated. The residual oil crystallized from benzene/hexane to give 3,4-dimethoxyphenyl-2-pyridyl carbinol, mp 92°–94°.

A stirred suspension of 12.3 g (0.05 M) of the above carbinol in 150 ml of water was heated to 70° and 11.9 g (0.075 m) of potassium permanganate added in portions. The mixture was stirred and heated at 80°–90° for 1 hour, cooled to 30° and diluted with 150 ml of ethyl acetate. This mixture was filtered and the organic extract was dried and concentrated to give 3,4-dimethoxyphenyl-2-pyridyl ketone, mp 92°–93° C.

A solution of 12.5 g of the above ketone in 120 ml of 48% HBr was refluxed for 2 hours, then concentrated in vacuo, dissolved in ethanol, toluene added, the solution concentrated, and the residue stripped from toluene to give 3,4-dihydroxyphenyl-2-pyridyl ketone hydrobromide. Treatment of this crude hydrobromide with aqueous sodium bicarbonate followed by extraction with ethyl acetate yielded 3,4-dihydroxyphenyl-2-pyridyl ketone, mp 174°–176°.

A solution of sodium hydroxide (from 4.3 g of sodium hydroxide in 8 ml of water) was added to a solution of 10.7 g (0.05 M) of the above ketone in 250 ml of 1-butanol. The resulting mixture was stirred under nitrogen for 10 minutes and then treated with 13.8 g (0.05 m) of 1,14-dichloro-3,6,9,12-tetraoxatetradecane. After refluxing for 24 hours, the mixture was cooled to 35°, filtered through celite and concentrated to give a dark oil, which was dissolved in chloroform, washed with 2% NaOH and then with water. The chloroform solution was dried and concentrated to give a viscous oil. Continuous ether extraction of this oil gave 1-(2,3,5,6,8,9,11,12,14,15-decahydro-1,4,7,10,13,16-benzohexaoxacyclooctadecin-18-yl)-1-(2-pyridyl)-methanone, mp 78°–80°.

EXAMPLE 41

4'-(3-Pyridylcarbonyl)benzo-18-crown-6, also named 1-(2,3,5,6,8,9,11,12,14,15-decahydro-1,4,7,10,13,16-benzohexaoxacyclooctadecin-18-yl)-1-(3-pyridyl)-methanone 3,4-Dimethoxyphenyl-3-pyridyl carbinol was obtained as an oil as described for the preceding 2-pyridyl carbinol of Example 40 except that 3-bromopyridine is used in place of 2-bromopyridine. This carbinol was converted to 3,4-dimethoxyphenyl-3-pyridyl ketone, mp 76°–78° C and reacted with hydrobromic acid to give 3,4-dihydroxyphenyl-3-pyridyl ketone, mp 182°–184° Crown ether formation as described in Example 40 gave 1-(2,3,5,6,8,9,11,12,14,15-decahydro-1,4,7,10,13,16 hexaoxacyclooctadecin-18-yl)-1-(3-pyridyl)-methanone, mp 98°–100° C.

Additional compounds of the invention are shown in Tables II and III. The compounds of Examples 47, 48 and 54 were obtained by nitration of Example 1, 45 and 2 by 10–18% excess NaNO$_2$ in CF$_3$COOH. The compound of Example 49 was obtained by heating 7.98 g of AlCl$_3$, 9.77 g of phthalic anhydride and 3.12 of benzo-18-crown-6 in 80 ml of 1,2-dichloroethylene and 25 ml of nitrobenzene at 70° for 16 hours. The product was steam distilled and the residue extracted with CH$_2$Cl$_2$, then with 2N NaOH followed by acidification to give an oil which crystallized from ethyl acetate.

TABLE II

| Example | Ar (4'-Position) | R (5'-Position) | (Q=benzo) mp° C | Elemental Analysis For | Calcd. | Found |
|---|---|---|---|---|---|---|
| 42 |  | CH$_3$ | 97–98 | Nmr(CDCl$_3$): δ 2.25 [2H]s(CH$_3$), δ 3.4–4.5 [20H]m(CH$_2$O), δ 6.95 [1H]s(aromatic), δ 7.05 [1H]s(aromatic), δ 7.5–7.8 [1H]m (pyridyl), δ 8.48–8.56 [1H]d(pyridyl) | | |
| 43 | 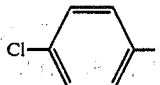 | CH$_3$ | 85–95 (Monohydrate) | C H Cl | 55.71 5.84 13.70 | 55.90, 56.18 5.90, 5.95 |
| 44 |  | CH$_3$ | 96–97 | C H Cl | 62.60 6.29 7.63 | 62.17, 61.88 6.31, 6.34 7.64 |
| 45 | 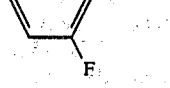 | H | 117.8–119.3 | C H F | 63.58 6.27 4.37 | 63.78 6.42 5.06 |
| 46 | 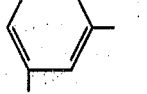 | CH$_3$ | 96–98 | C H Br | 56.59 5.74 15.69 | 56.82, 56.98 5.84, 5.78 15.31 |
| 47 | 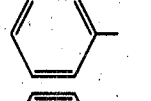 | NO$_2$ | 151.4–153.8 | C H N | 59.86 5.90 3.04 | 60.02 6.01 3.24 |
| 48 | 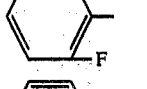 | NO$_2$ | 124.0–125.2 | | | |
| 49 | 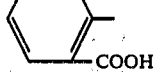 | H | 70–78 (Hemihydrate) | C H | 61.13 6.62 | 60.56, 61.32 6.46, 6.60 |

TABLE II-continued

| | Ar | R | (Q=benzo) | Elemental Analysis | | |
|---|---|---|---|---|---|---|
| Example | (4'-Position) | (5'-Position) | mp° C | For | Calcd. | Found |
| 50 | Cl-[phenyl]-Cl | CH₃ | 103–104.5 | C<br>H<br>Cl | 57.72<br>5.65<br>14.20 | 57.80, 57.84<br>5.62, 5.74 |
| 51 | F-[phenyl]- | CH₃(3'-position) | bp 226–232/<br>0.1 mm | Nmr(CDCl₃): δ 2.35 [3H]s(CH₃), δ 3.6–4.6 [20H]m(CH₂O), δ 6.7–7.4 [4H]m(aromatic), δ 7.7–8.0 [2H]m(aromatic) | | |
| 52 | [pyridyl with N at 2-position]- | CH₃(3'-position) | | | | |
| 53 | [pyridyl with N at 3-position]- | CH₃(3'-position) | | | | |
| 54 | Cl-[phenyl]- | NO₂ | 132.5–134.5 | C<br>H<br>N | 55.71<br>5.28<br>2.82 | 55.65<br>5.17<br>2.74 |

TABLE III

| | | (n=o & Q=benzo) | |
|---|---|---|---|
| Example | Ar(3¹-Position) | mp° C (or/bp) | 60mc Nmr* |
| 55 | [pyridyl, N at 2]- | bp 208–216/0.15 mm | (CDCl₃) δ 3.4–4.5 [20H]m(CH₂O),<br>δ 6.9–7.6 [4H]m(aromatic and pyridyl),<br>δ 7.9–8.2 [1H]m(pyridyl),<br>δ 8.5–8.7 [2H]m(pyridyl) |
| 56 | [pyridyl, N at 3]- | bp 205–215/0.1 mm | (CDCl₃) δ 3.4–4.4 [20H]m(CH₂O),<br>δ 6.9–7.7 [5H]m(aromatic and pyridyl)<br>δ 8.5–8.7 [2H]m(pyridyl) |
| 57 | C₆H₅— | bp 215/220/0.15 mm | (CDCl₃) δ 3.0–4.2 [20H]m(CH₂O),<br>δ 6.7–7.9 [8H]m(aromatic) |
| 58 | [pyridyl, N at 4]- | mp 75.–6 | (DMSO-d₆) δ 3.0–4.2 [20H]m(CH₂O),<br>δ 6.9–7.2 [3H]m(aromatic)<br>δ 7.2–7.4 [1H]m(aromatic),<br>δ 7.9–8.1 [2H]m(pyridyl),<br>δ 8.25–8.4 [1H]d(pyridyl) |

*Solvent-CHCl₃ is deuteriochloroform; DMSO-d₆ is hexadeuterodimethylsulfoxide
δ is downfield shifts from tetramethylsilane in ppm. Square brackets is the integrated proton count for resonance. d = doublet, m = multiplet, s = singlet Parenthesis assignment of resonance.

EXAMPLE 59

5'-Amino-4'-benzoylbenzo-18-crown-6

4'-Benzoyl-5'-nitrobenzo-18-crown-6 (0.53 g — See Example 47) was dissolved in 125 ml of warm ethanol, 0.2 g of platinum oxide was added and the mixture was hydrogenated at 40 psi using a Parr Pressure Reaction Apparatus. After 4 hr the reaction bottle was vented, the resulting mixture was filtered, and the filtrate was evaporated under reduced pressure to give 0.50 g of a yellow oil. The yellow oil exhibited high antiviral activity against human rhinoviruses.

The oil exhibited infrared absorptions at 3350 and 3450 cm⁻¹ (amino) and at 1640 cm⁻¹ (aromatic ketone).

This oil (0.4 g) was dissolved in 3 ml of ethanol, concentrated hydrochloric acid was added to pH 3, the solution was filtered, and 200 ml of ether was added quickly to the filtrate. The resulting yellow crystalline hydrochloride (0.36 g) was separated by filtration and washed with ether. It melted at 58° with decomposition.

EXAMPLE 60

5'-Amino-4'-o-fluorobenzoylbenzo-18-crown-6

4'-o-Fluorobenzoyl-5"-nitrobenzo-18-crown-6 (1.09 g - See Example 48) was hydrogenated with 60 mg of platinum oxide in 150 ml of warm ethanol. After processing as in the above example, the resulting yellow oil weighed 1.025 g.

The compound exhibited infrared absorptions at 3380 and 3460 cm⁻¹ (amino) and at 1640 cm⁻¹ (aromatic ketone).

EXAMPLE 61

5'-Amino-4'-p-chlorobenzoylbenzo-18-crown-6

A mixture of 0.5 g of 4'-p-chlorobenzoyl-5'-nitrobenzo-18-crown-6 in 200 ml of ethanol and 100 mg of 5% platinum on charcoal was hydrogenated at 55 psi on a Parr hydrogenation apparatus. The resulting solution was filtered, stripped of solvent to leave 0.41 g of yellow oil which exhibited infrared absorptions at 3400 and 3500 cm$^{-1}$ (amino) and 1640 cm$^{-1}$ (aromatic ketone). This compound was dissolved in a small amount of ethanol, concentrated hydrochloric acid was added dropwise to pH 2. Then 300 ml of ether was added quickly and the resulting mixture was filtered to give 0.3 g of yellow solid hydrochloride.

Most of the compounds exhibit significant antiviral activity against all strains of human rhinoviruses when tested in tissue culture experiments as follows:

Cultured cells (usually HeLa, a human cell line) are grown to confluency in 60 mm plastic petri dishes. Each culture is then infected with approximately 300 plaque-forming units of virus. Three different rhinovirus types (1A, 2, and 14) were used in all tests. The virus is allowed to adsorb to the cells for 30 minutes at 34.5° C.

Meanwhile, the compounds to be tested are dissolved in either ethanol or dimethylsulfoxide at a concentration 100 times greater than the highest concentration to be used in the test. (Compounds are tested in two-fold dilution steps from 200–12.5 μg/ml, but some compounds have been tested as low as 0.1 μg/ml.) The compound solution is then diluted 1:100 into a solution of McCoy's medium containing 5% heat-inactivated fetal calf serum and 0.38% agar. Two-fold dilutions are then made in the agar medium.

After the virus has adsorbed to the cells, excess virus is washed off and the cultures are overlaid with 5 ml of the agar medium containing the different compound concentrations. A control culture receives only agar medium. The cultures are incubated at 34.5° C for two to five days, depending on the virus used, to allow the development of plaques.

A plaque is a roughly circular area of dead cells in the culture, indicating the area where one plaque-forming unit of virus first infected one cell. The agar gel restricts the mobility of the virus so that the infection is contained and spreads out only from infected cell to neighboring cell.

When the plaques in the control culture are large enough to be seen easily but are still fairly discrete, all of the cultures are stained with 1% crystal violet. The plaques appear as clear spots against the deep purple of the uninfected cells. Toxic doses of compound will cause cells to detach from the plate and the cultures will take up less stain than the control culture. The compound-treated cultures are compared to the control culture for toxicity and for inhibition of plaques.

The activity level is the concentration of test chemical at which plaques are greatly reduced in size and number but are still partially visible (the virus "breakthrough" point). The toxicity level is the concentration of test chemical at which there is less intensity of purple color of the stained cultures compared to the controls.

The following table shows antiviral activity/cytotoxicity in microgram per ml of compounds of examples specified.

TABLE IV

Activity of Crown Compounds Against Human Rhinovirus (HRV)
Activity/Toxicity (μg/ml)

| Ex. | HRV-1A | HRV-2 | HRV-14 |
|---|---|---|---|
| 1 | 10/50 | 2/50 | 5/50 |
| 2 | 5/20 | 2/20 | 2/20 |
| 3 | 5/10 | 2/10 | 2/10 |
| 4 | 20/50 | 20/50 | 20/50 |
| 5 | 1/50 | 0.5/50 | 1/50 |
| 6 | 1/5 | 1/5 | 1/5 |
| 7 | >10/10 | >10/10 | >10/10 |
| 8 | >10/10 | >5/10 | >10/10 |
| 9 | 1/20 | >1/20 | 1/20 |
| 10 | 5/10 | 2/10 | 2/10 |
| 11 | >10/20 | 10/20 | >10/20 |
| 12 | 5/10 | 2/10 | 2/10 |
| 13 | >2/5 | >2/5 | >2/5 |
| 14 | 2/5 | 2/5 | >2/5 |
| 15 | >2/5 | 2/5 | >2/5 |
| 16 | 20/50 | 20/50 | 20/50 |
| 17 | 1/20 | 1/20 | 2/20 |
| 18 | 10/>100 | 5/>100 | 5/>100 |
| 19 | 5/200 | 2/200 | 5/200 |
| 20 | 5/20 | >5/20 | 5/20 |
| 21 | 5/10 | 2/10 | 5/10 |
| 22 | 0.5/5 | 0.5/5 | 1/5 |
| 23 | 5/100 | 2/100 | 2/100 |
| 24 | 1/5 | 0.5/5 | 1/5 |
| 25 | 0.5/100 | 0.2/100 | 0.2/100 |
| 26 | 5/10 | 5/10 | 5/10 |
| 27 | 5/20 | 2/20 | 2/20 |
| 28 | 2/50 | 1/50 | 2/50 |
| 29 | 0.5/20 | 0.2/20 | 0.5/20 |
| 30 | 1/>20 | 0.5/>20 | 0.5/>20 |
| 31 | 0.5/10 | 1.2/10 | 1.2/10 |
| 32 | 2/10 | 1/10 | 2/10 |
| 33 | 0.5/5 | 0.2/5 | 0.5/5 |
| 34 | 2/50 | 0.5/>10 | 2/10 |
| 35 | 1/10 | — | 1/10 |
| 36 | 2/10 | 1/10 | 1/10 |
| 37 | 2/5 | 2/5 | 2/5 |
| 38 | 2/10 | 1/10 | 2/10 |
| 39 | 10/20 | 10/20 | 10/20 |
| 40 | 50/>200 | 20/>200 | 20/>200 |
| 41 | 20/>200 | 10/>200 | 20/>200 |
| 42 | 10/20 | — | 5/20 |
| 43 | 1/5 | 0.5/5 | 0.5/5 |
| 44 | 0.5/5 | 0.2/5 | 0.5/5 |
| 45 | 20/60 | 10/50 | 10/50 |
| 46 | 0.5/2 | 0.2/2 | 0.5/2 |
| 50 | 5/10 | 5/10 | 2/10 |
| 51 | — | — | >2/5 |
| 58 | 2/50 | 1/50 | 2/50 |
| 59 | 2/50 | 1/50 | 2/50 |
| 60 | 5/50 | 2/50 | 5/50 |
| 61 | 2/20 | 1/20 | 1/20 |

In vitro (tissue culture) activity has also been demonstrated against polio, coxsackie A21, B1, and human rhinovirus (including 1A, 1B, 2, 3, 5, 13, 14, 15, 39, 41, 51, 998, 1426, 1492, 1662, 4006 and 6579). The compounds of this invention can therefore be used at concentrations of 1 to 200 micrograms per ml in aqueous media, preferably with a surfactant, to decontaminate the in vitro habitat on which such viruses are present, including surfaces such as laboratory glassware, laboratory containers, laboratory working surfaces and similar areas in research laboratories and hospitals, etc.

The following table shows activities of representative compounds against polio 2 and coxsackie A21 virus when tested by the method given earlier.

TABLE V

| Compound of Example | Activity/Toxicity (μg/ml) | |
|---|---|---|
| | Polio-2 | Coxsackie-A21 |
| 9 | 5/50 | 5/50 |
| 23 | 2/>50 | 2/>50 |
| 24 | 1/>5 | 1/>5 |
| 28 | 2/>10 | 5/>10 |
| 29 | 1/75 | 1/75 |
| 33 | 1/5 | 1/5 |
| 35 | 1/10 | 1/10 |

The use of the compounds of the invention to form dispersions of carbon black or powdered charcoal in water is shown as follows:

10 mg of "Vulcan" 3-R carbon black, an oil furnace carbon black sold by Cabot Corp., were placed in each of three 15 × 45 mm vials. Two ml of water was added to the first vial.

A solution of 5 mg of 18-benzoyl-2,3,5,6,8,9,11,12,14,15-decahydro-1,4,7,10,13,16-benzohexaoxacyclooctadecin(4'-benzoyl-benzo-18-crown-6, Example 6) in 0.1 ml of dimethylsulfoxide was added to 2.0 ml of water in the second vial.

Two ml of water and 0.1 ml of dimethyl sulfoxide was added to the third vial.

Five microliters of a commercial surfactant solution (Kodak Photo-Flo) was added to each vial.

All vials were shaken. In all cases uniform black suspensions were obtained.

The vials were then allowed to stand and were observed periodically. After 10 minutes most of the black particles had settled out of upper half of the first and third (control) vials. The second vial containing the benzo-18-crown-6 compound of this invention remained completely opaque.

After 3 days nearly all solids had settled out of the first and third vials. Only partial settling was observable in the top quarter of the second vial. Thus the settling out of suspended particles in the second (test) vial in 3 days (72 hours) was less than had occurred in the two control vials in 10 minutes: i.e., the rate of settling had been decreased by more than a factor of 400 times.

The above general procedure was used with other crown ether ketones and the time required for a red line on paper ¼ inch below the liquid meniscus level to become visible was noted. When no crown dispersant was added only 5 minutes was required. When the compound of Example 57 was used, 20 hrs was needed while with the compound of Example 55, 96 hrs was required.

The nomenclature used by Chemical Abstracts is based on the following ring numbering system and the compound of Example 3, for instance, would be named 18-(4'-fluorobenzoyl)-2,3,5,6,8,9,11,12,14,15-decahydro-1,4,7,10,13,16-benzohexaoxacyclooctadecin or as (2,3,5,6,8,9,11,12,14,15-decahydro-1,4,7,10,13,16-benzohexaoxacyclooctadecin-18-yl)(4-fluorophenyl)-methanone.

I claim:
1. A compound of the formula wherein
Ar is thienyl, pyridyl or furyl, each with up to two substituents of alkyl of 1-10 carbons, alkoxy of 1-10 carbons, halogen, carboxy or cyano groups;
Q is in which R is fluorine, chlorine, bromine, nitro, amino, or alkyl of 1-10 carbons; and $n$ is 0 to 2.
2. A compound of claim 1 wherein R is $CH_3$.
3. A compound of claim 1 wherein R is $NH_2$.
4. A compound of claim 1 wherein R is H.
5. The compound of claim 2 wherein Ar is 2-thienyl.
6. The compound of claim 2 wherein Ar is 2-furyl.
7. The compound of claim 2 wherein Ar is 3-furyl.
8. The compound of claim 1 wherein Ar is 2-methyl-5-thienyl.
9. The compound of claim 1 which is 4'-(3-pyridylcarbonyl)-3'-methylbenzo-18-crown-6.
10. The compound of claim 1 which is 4'-(3-furoylcarbonyl)-5'-methylbenzo-18-crown-6.
11. The compound of claim 1 which is 4'-[2-(5-methylthienyl)carbonyl]-5'-methylbenzo-18-crown-6.
12. The compound of claim 1 wherein Ar is thienyl.
13. The compound of claim 1 wherein Ar is pyridyl.
14. The compound of claim 1 wherein Ar is furyl.

* * * * *